(12) United States Patent
Christensen et al.

(10) Patent No.: US 8,177,772 B2
(45) Date of Patent: May 15, 2012

(54) CATHETER CONNECTION SYSTEMS

(75) Inventors: Mark A. Christensen, Salt Lake City, UT (US); William Randy Barron, Riverton, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1286 days.

(21) Appl. No.: 11/535,245

(22) Filed: Sep. 26, 2006

(65) Prior Publication Data

US 2007/0073270 A1     Mar. 29, 2007

Related U.S. Application Data

(60) Provisional application No. 60/720,443, filed on Sep. 26, 2005.

(51) Int. Cl.
*A61M 25/16* (2006.01)
*A61M 5/00* (2006.01)

(52) U.S. Cl. ........ 604/533; 604/534; 604/535; 604/536; 604/246; 604/256

(58) Field of Classification Search .......... 604/533–539, 604/244, 246, 256; 285/33
See application file for complete search history.

(56) References Cited

U.S. PATENT DOCUMENTS

| | | |
|---|---|---|
| 3,003,500 A | 10/1961 | Barton et al. |
| 3,021,841 A | 2/1962 | Burke ........................... 604/185 |
| 3,115,138 A | 12/1963 | McElvenny et al. |
| 3,223,610 A | 12/1965 | Inoue |
| 3,233,610 A | 2/1966 | Wade |
| 3,241,554 A | 3/1966 | Coanda |
| 3,253,594 A | 5/1966 | Matthews |
| 3,312,221 A | 4/1967 | Overment |
| 3,363,626 A | 1/1968 | Bidwell et al. |
| 3,376,868 A | 4/1968 | Mondiadis |
| 3,417,750 A | 12/1968 | Carson .......................... 604/185 |
| 3,419,010 A | 12/1968 | Williamson |
| 3,459,189 A | 8/1969 | Alley |
| 3,487,837 A | 1/1970 | Petersen |
| 3,542,026 A | 11/1970 | Bledsoe |
| 3,554,580 A | 1/1971 | Goyke |
| 3,566,875 A | 3/1971 | Stoehr .............................. 604/9 |
| 3,572,340 A | 3/1971 | Lloyd et al. .................... 604/133 |

(Continued)

FOREIGN PATENT DOCUMENTS

DE        1616493 A1    6/1971

(Continued)

OTHER PUBLICATIONS

Bellamy, R.F., "The Cause of Death in Conventional Land Warfare: Implications for Combat Casualty Care Research." Mil. Med., vol. 149, pp. 55-62, 1984.

(Continued)

*Primary Examiner* — Kevin C Sirmons
*Assistant Examiner* — Bradley Thomas, Jr.
(74) *Attorney, Agent, or Firm* — Rutan & Tucker, LLP

(57) ABSTRACT

A catheter connection system is disclosed. In one embodiment, a catheter connection system may include at least two components and a deformable sealing element positioned between the at least two components configured to allow, upon deformation, fluid flow through the at least two components. In another embodiment, the catheter connection system may include a sealing element positioned between at least two components, wherein the components are coupled to one another by a locking member.

10 Claims, 4 Drawing Sheets

U.S. PATENT DOCUMENTS

| | | | |
|---|---|---|---|
| 3,650,507 A | 3/1972 | Nyberg et al. | |
| 3,680,562 A | 8/1972 | Wittes et al. | |
| 3,683,929 A | 8/1972 | Holter | |
| 3,742,952 A | 7/1973 | Magers et al. | |
| 3,752,158 A | 8/1973 | Kariher | |
| 3,768,476 A | 10/1973 | Raitto | |
| 3,774,611 A | 11/1973 | Tussey et al. | |
| 3,777,757 A | 12/1973 | Gray et al. | |
| 3,783,870 A | 1/1974 | Schachet | |
| 3,820,546 A | 6/1974 | Chittenden et al. | |
| 3,853,127 A | 12/1974 | Spademan | |
| 3,920,023 A | 11/1975 | Dye et al. | |
| 3,960,153 A | 6/1976 | Carey et al. | |
| 3,982,546 A | 9/1976 | Friend | |
| 4,022,209 A | 5/1977 | Nehring | |
| 4,029,095 A | 6/1977 | Pena | |
| 4,105,031 A | 8/1978 | Kurtz et al. | |
| 4,112,949 A | 9/1978 | Rosenthal et al. | |
| 4,116,366 A | 9/1978 | Takenakashima et al. | |
| 4,120,715 A | 10/1978 | Ockwell et al. | |
| 4,136,696 A | 1/1979 | Nehring | |
| 4,143,853 A | 3/1979 | Abramson | |
| 4,153,058 A | 5/1979 | Nehme | |
| 4,174,053 A | 11/1979 | Shimizu | |
| 4,187,848 A | 2/1980 | Taylor | 604/243 |
| 4,203,445 A | 5/1980 | Jessup et al. | |
| 4,214,593 A | 7/1980 | Imbruce et al. | |
| 4,257,629 A | 3/1981 | Maple et al. | 285/12 |
| 4,265,848 A | 5/1981 | Rusch | |
| 4,266,355 A | 5/1981 | Moss | |
| 4,266,355 A | 5/1981 | Moss | |
| 4,310,104 A | 1/1982 | Takatsuki | |
| 4,315,513 A | 2/1982 | Nawash et al. | |
| 4,334,551 A | 6/1982 | Pfister | |
| 4,341,212 A | 7/1982 | Medwid | |
| D267,433 S | 12/1982 | Pageau | |
| 4,364,395 A | 12/1982 | Redmond et al. | |
| D267,815 S | 2/1983 | Elliott et al. | |
| 4,382,442 A | 5/1983 | Jones | |
| 4,392,858 A | 7/1983 | George et al. | |
| 4,393,873 A | 7/1983 | Nawash et al. | |
| 4,427,425 A | 1/1984 | Briggs et al. | |
| 4,433,973 A | 2/1984 | Kurtz et al. | |
| 4,439,190 A | 3/1984 | Protzmann et al. | |
| 4,447,235 A | 5/1984 | Clarke | 604/167.02 |
| 4,455,141 A | 6/1984 | Todd | |
| 4,464,168 A | 8/1984 | Redmond et al. | |
| 4,475,904 A | 10/1984 | Wang | |
| 4,479,818 A | 10/1984 | Briggs et al. | |
| 4,490,003 A | 12/1984 | Robinson | |
| 4,496,464 A | 1/1985 | Hensley | |
| 4,511,163 A | 4/1985 | Harris et al. | 285/148.16 |
| 4,512,771 A | 4/1985 | Norton | |
| 4,525,167 A | 6/1985 | Goldberg et al. | |
| 4,543,100 A | 9/1985 | Brodsky | |
| 4,564,222 A | 1/1986 | Loker et al. | 285/243 |
| 4,569,674 A | 2/1986 | Phillips et al. | |
| 4,605,400 A | 8/1986 | Kurtz et al. | |
| 4,610,469 A | 9/1986 | Wolff-Mooij | |
| 4,610,671 A | 9/1986 | Luther | |
| 4,620,846 A | 11/1986 | Goldberg et al. | |
| 4,643,720 A | 2/1987 | Lanciano | |
| 4,648,870 A | 3/1987 | Goldberg et al. | |
| 4,666,433 A | 5/1987 | Parks | |
| 4,669,463 A | 6/1987 | McConnell | 128/207.14 |
| 4,673,398 A | 6/1987 | Turner et al. | |
| 4,675,020 A | 6/1987 | McPhee | |
| 4,681,571 A | 7/1987 | Nehring | 604/320 |
| 4,685,901 A | 8/1987 | Parks | |
| 4,685,908 A | 8/1987 | Kurtz | |
| 4,701,163 A | 10/1987 | Parks | |
| 4,702,733 A | 10/1987 | Wright et al. | |
| 4,706,830 A | 11/1987 | Wareing et al. | |
| 4,722,735 A | 2/1988 | Brodmann | |
| 4,738,671 A | 4/1988 | Elliott et al. | |
| 4,740,202 A | 4/1988 | Stacey et al. | |
| 4,741,678 A | 5/1988 | Nehring | 471/395 |
| 4,747,843 A | 5/1988 | Felix et al. | |
| 4,747,844 A | 5/1988 | Elliott | |
| 4,752,292 A * | 6/1988 | Lopez et al. | 604/244 |
| 4,758,238 A | 7/1988 | Sundblom et al. | |
| 4,781,674 A | 11/1988 | Redmond et al. | 604/9 |
| 4,790,567 A | 12/1988 | Kawano et al. | |
| 4,809,679 A | 3/1989 | Shimonaka et al. | |
| 4,813,929 A | 3/1989 | Semrad | |
| 4,820,288 A | 4/1989 | Isono | |
| 4,832,442 A | 5/1989 | Pappas | |
| 4,834,702 A | 5/1989 | Rocco | |
| 4,844,087 A | 7/1989 | Garg | 600/566 |
| 4,850,955 A | 7/1989 | Newkirk | |
| 4,857,042 A | 8/1989 | Schneider | |
| 4,863,593 A | 9/1989 | Quick | |
| 4,867,740 A | 9/1989 | East | |
| 4,874,377 A | 10/1989 | Newgard et al. | 604/167.02 |
| 4,883,474 A | 11/1989 | Sheridan et al. | |
| 4,883,476 A | 11/1989 | Kurtz et al. | |
| 4,921,488 A | 5/1990 | Maitz et al. | |
| 4,929,235 A | 5/1990 | Merry et al. | 604/167.04 |
| 4,930,997 A | 6/1990 | Bennett | |
| 4,944,732 A | 7/1990 | Russo | 604/247 |
| 4,946,448 A | 8/1990 | Richmond | |
| 4,946,449 A | 8/1990 | Davis, Jr. | 604/256 |
| 4,949,756 A | 8/1990 | Melinyshyn et al. | |
| 4,950,256 A | 8/1990 | Luther et al. | |
| 4,960,412 A | 10/1990 | Fink | 604/167.04 |
| 4,966,197 A | 10/1990 | Jaron et al. | |
| 4,968,294 A | 11/1990 | Salama | |
| 4,969,879 A | 11/1990 | Lichte | 604/533 |
| 4,969,890 A | 11/1990 | Sugita et al. | |
| 4,973,311 A | 11/1990 | Iwakoshi et al. | |
| 4,995,864 A | 2/1991 | Bartholomew et al. | |
| 5,009,636 A | 4/1991 | Wortley et al. | 604/43 |
| 5,019,096 A | 5/1991 | Fox, Jr. et al. | |
| 5,037,403 A | 8/1991 | Garcia | |
| 5,052,998 A | 10/1991 | Zimmon | |
| 5,053,014 A * | 10/1991 | Van Heugten | 604/167.03 |
| 5,057,084 A | 10/1991 | Ensminger et al. | 604/167.04 |
| 5,061,255 A | 10/1991 | Greenfeld et al. | |
| 5,064,416 A | 11/1991 | Newgard et al. | 604/167.03 |
| 5,078,677 A | 1/1992 | Gentelia et al. | |
| 5,078,689 A | 1/1992 | Keller | 604/167.02 |
| 5,078,699 A | 1/1992 | Haber et al. | |
| 5,092,850 A | 3/1992 | Buma | |
| 5,098,405 A | 3/1992 | Peterson et al. | 604/247 |
| 5,100,394 A | 3/1992 | Dudar et al. | |
| 5,102,404 A | 4/1992 | Goldberg et al. | |
| 5,106,054 A | 4/1992 | Mollenauer et al. | 251/149.1 |
| 5,112,323 A | 5/1992 | Winkler et al. | 604/319 |
| 5,137,524 A | 8/1992 | Lynn et al. | |
| 5,141,499 A | 8/1992 | Zappacosta | |
| 5,156,597 A | 10/1992 | Verreet et al. | |
| 5,165,953 A | 11/1992 | Shlenker et al. | |
| 5,188,622 A | 2/1993 | Muller et al. | |
| 5,199,946 A | 4/1993 | Abramowitz | |
| 5,207,655 A | 5/1993 | Sheridan | 604/247 |
| 5,215,538 A | 6/1993 | Larkin | |
| 5,234,454 A | 8/1993 | Bangs | |
| 5,238,217 A | 8/1993 | Fell | |
| 5,251,873 A | 10/1993 | Atkinson et al. | |
| 5,261,897 A | 11/1993 | Kurtz et al. | |
| 5,269,771 A * | 12/1993 | Thomas et al. | 604/539 |
| 5,279,551 A | 1/1994 | James | 604/44 |
| 5,295,657 A | 3/1994 | Atkinson | |
| 5,295,658 A | 3/1994 | Atkinson et al. | |
| 5,300,034 A | 4/1994 | Behnke et al. | |
| 5,300,048 A | 4/1994 | Drewes, Jr. et al. | |
| 5,304,121 A | 4/1994 | Sahatjian | |
| 5,320,110 A | 6/1994 | Wang | |
| 5,322,518 A | 6/1994 | Schneider et al. | 604/247 |
| 5,334,166 A | 8/1994 | Palestrant | |
| 5,344,401 A | 9/1994 | Radisch et al. | |
| 5,352,198 A | 10/1994 | Goldenberg et al. | |
| 5,356,391 A | 10/1994 | Stewart | |
| 5,360,413 A | 11/1994 | Leason et al. | |
| 5,390,898 A | 2/1995 | Smedley et al. | |
| 5,395,651 A | 3/1995 | Sodervall et al. | |
| 5,399,165 A | 3/1995 | Paul, Jr. | |

| | | | | | | |
|---|---|---|---|---|---|---|
| 5,401,245 A | 3/1995 | Haining | | 6,103,695 A | 8/2000 | Lane et al. |
| 5,405,331 A | 4/1995 | Behnke et al. | | 6,106,502 A | 8/2000 | Richmond |
| 5,423,334 A | 6/1995 | Jordan | | 6,106,503 A | 8/2000 | Pfeiderer et al. |
| 5,435,470 A | 7/1995 | Kim | | 6,113,068 A | 9/2000 | Ryan |
| 5,437,900 A | 8/1995 | Kuzowski | | 6,117,114 A | 9/2000 | Paradis |
| 5,456,675 A | 10/1995 | Wolbring et al. ............ 604/280 | | 6,129,699 A | 10/2000 | Haight et al. |
| 5,465,857 A | 11/1995 | Yang | | 6,129,750 A | 10/2000 | Tockman et al. |
| 5,470,319 A | 11/1995 | Mayer | | 6,132,403 A | 10/2000 | Lopez |
| 5,472,325 A | 12/1995 | Svendsen ................ 417/437 | | 6,132,407 A | 10/2000 | Genese et al. |
| 5,472,435 A | 12/1995 | Sutton | | 6,149,129 A | 11/2000 | Harris et al. ............ 251/149.1 |
| 5,480,392 A | 1/1996 | Mous | | 6,156,004 A | 12/2000 | Tremaine et al. ............ 604/27 |
| 5,484,401 A | 1/1996 | Rodriguez et al. ............ 604/28 | | 6,165,217 A | 12/2000 | Hayes |
| 5,489,269 A | 2/1996 | Aldrich et al. | | 6,168,137 B1 | 1/2001 | Paradis ................ 251/149.6 |
| 5,492,304 A | 2/1996 | Smith et al. | | 6,170,800 B1 | 1/2001 | Meloul et al. ............ 251/149.1 |
| 5,496,299 A | 3/1996 | Felix et al. | | 6,171,287 B1 | 1/2001 | Lynn et al. |
| 5,501,426 A | 3/1996 | Atkinson et al. | | 6,193,682 B1 | 2/2001 | Ahmed |
| 5,507,733 A | 4/1996 | Larkin et al. | | 6,196,992 B1 | 3/2001 | Keilman et al. |
| 5,507,847 A | 4/1996 | George et al. | | 6,200,292 B1 | 3/2001 | French et al. ............ 604/131 |
| 5,509,433 A | 4/1996 | Paradis | | 6,217,556 B1 | 4/2001 | Ellingson et al. |
| 5,509,909 A | 4/1996 | Moy | | 6,221,425 B1 | 4/2001 | Michal et al. |
| 5,509,912 A | 4/1996 | Vaillancourt et al. | | 6,234,992 B1 | 5/2001 | Haight et al. |
| 5,514,117 A | 5/1996 | Lynn | | 6,245,048 B1 | 6/2001 | Fangrow, Jr. et al. |
| 5,520,665 A | 5/1996 | Fleetwood et al. | | 6,254,061 B1 | 7/2001 | Levine et al. |
| 5,529,278 A | 6/1996 | Weldon et al. | | 6,254,581 B1 | 7/2001 | Scott |
| 5,535,785 A | 7/1996 | Werge et al. | | 6,261,282 B1 | 7/2001 | Jepson et al. |
| 5,540,661 A | 7/1996 | Tomisaka et al. | | 6,283,949 B1 | 9/2001 | Roorda |
| 5,556,387 A | 9/1996 | Mollenauer et al. | | 6,287,285 B1 | 9/2001 | Michal et al. |
| 5,573,516 A | 11/1996 | Tyner | | 6,299,131 B1 | 10/2001 | Ryan |
| 5,576,072 A | 11/1996 | Hostettler et al. | | 6,299,593 B1 | 10/2001 | Wakabayashi ............ 604/48 |
| 5,628,908 A | 5/1997 | Kamen et al. ............ 210/646 | | 6,309,423 B2 | 10/2001 | Hayes |
| 5,636,875 A | 6/1997 | Wasser et al. | | 6,328,765 B1 | 12/2001 | Hardwick et al. |
| 5,662,960 A | 9/1997 | Hostettler et al. | | 6,332,892 B1 | 12/2001 | Desmond, III et al. |
| 5,674,192 A | 10/1997 | Sahatjian et al. | | 6,344,033 B1 * | 2/2002 | Jepson et al. ............ 604/256 |
| 5,676,346 A | 10/1997 | Leinsing | | 6,375,024 B1 | 4/2002 | Park |
| D385,889 S | 11/1997 | Kullas et al. | | 6,391,009 B1 | 5/2002 | Crosa Dorado et al. |
| 5,685,866 A | 11/1997 | Lopez | | 6,409,716 B1 | 6/2002 | Sahatjian et al. |
| 5,701,934 A | 12/1997 | Kuran et al. | | 6,428,520 B1 | 8/2002 | Lopez et al. |
| 5,709,672 A | 1/1998 | Illner | | 6,447,473 B1 | 9/2002 | Levine et al. |
| 5,725,506 A | 3/1998 | Freeman et al. ........ 604/167.01 | | 6,482,190 B1 | 11/2002 | Genese et al. |
| 5,733,496 A | 3/1998 | Avellanet | | 6,491,668 B1 | 12/2002 | Paradis |
| 5,735,826 A | 4/1998 | Richmond | | 6,500,164 B1 | 12/2002 | Turner et al. |
| 5,738,144 A | 4/1998 | Rogers | | 6,530,951 B1 | 3/2003 | Bates et al. |
| 5,738,656 A | 4/1998 | Wagner et al. | | 6,541,116 B2 | 4/2003 | Michal et al. |
| 5,745,719 A | 4/1998 | Falcon et al. | | 6,551,267 B1 | 4/2003 | Cohen et al. |
| 5,746,719 A | 5/1998 | Farra et al. | | 6,554,808 B1 | 4/2003 | Cook |
| 5,776,119 A | 7/1998 | Bilbo et al. | | RE38,145 E | 6/2003 | Lynn |
| 5,792,098 A | 8/1998 | Felix et al. ................ 604/27 | | 6,626,418 B2 | 9/2003 | Kiehne et al. |
| 5,792,108 A | 8/1998 | Felix et al. ................ 604/131 | | 6,637,726 B2 | 10/2003 | Yamamoto |
| 5,807,348 A | 9/1998 | Zinger et al. | | 6,641,562 B1 | 11/2003 | Peterson |
| 5,810,792 A * | 9/1998 | Fangrow et al. ............ 604/533 | | 6,641,574 B2 | 11/2003 | Badia Segura et al. |
| 5,814,024 A | 9/1998 | Thompson et al. | | 6,645,547 B1 | 11/2003 | Shekalim et al. |
| 5,823,961 A | 10/1998 | Fields et al. | | 6,651,956 B2 | 11/2003 | Miller |
| 5,830,185 A | 11/1998 | Block, Jr. | | 6,652,484 B1 | 11/2003 | Hunckler et al. |
| 5,839,715 A | 11/1998 | Leinsing | | 6,655,655 B1 | 12/2003 | Matkovich et al. |
| 5,873,853 A | 2/1999 | Keilman et al. | | 6,656,517 B2 | 12/2003 | Michal et al. |
| 5,904,334 A | 5/1999 | Grunert et al. | | 6,665,888 B1 | 12/2003 | Kwak |
| 5,937,885 A | 8/1999 | Sampson | | 6,669,681 B2 | 12/2003 | Jepson et al. |
| 5,938,176 A | 8/1999 | Falconer | | 6,673,049 B2 | 1/2004 | Hommann et al. |
| 5,947,953 A | 9/1999 | Ash et al. | | 6,673,051 B2 | 1/2004 | Flinchbaugh |
| 5,954,706 A | 9/1999 | Sahatjian | | 6,695,817 B1 | 2/2004 | Fangrow, Jr. ............ 604/162.01 |
| 5,957,898 A | 9/1999 | Jepson et al. | | 6,699,213 B1 | 3/2004 | Annis et al. |
| 5,957,912 A | 9/1999 | Heitzmann | | 6,706,022 B1 | 3/2004 | Leinsing et al. |
| 5,961,497 A | 10/1999 | Larkin | | 6,719,991 B2 | 4/2004 | Darouiche et al. |
| 5,972,441 A | 10/1999 | Campbell et al. | | 6,726,672 B1 | 4/2004 | Hanly et al. |
| 5,976,650 A | 11/1999 | Campbell et al. | | 6,733,000 B2 | 5/2004 | McCarty et al. |
| 5,984,891 A | 11/1999 | Keilman et al. | | 6,745,998 B2 | 6/2004 | Doyle |
| 5,997,486 A | 12/1999 | Burek et al. ............ 600/573 | | 6,780,497 B1 | 8/2004 | Walter |
| 6,001,079 A | 12/1999 | Pourchez | | 6,802,836 B2 | 10/2004 | Bouphavichith et al. |
| 6,024,731 A | 2/2000 | Seddon et al. | | 6,808,161 B1 | 10/2004 | Hishikawa |
| 6,025,044 A | 2/2000 | Campbell et al. | | D500,132 S | 12/2004 | Peterson et al. |
| 6,027,779 A | 2/2000 | Campbell et al. | | D500,133 S | 12/2004 | Peterson et al. |
| 6,027,811 A | 2/2000 | Campbell et al. | | D500,552 S | 1/2005 | Peterson et al. |
| 6,029,946 A | 2/2000 | Doyle | | D500,853 S | 1/2005 | Peterson et al. |
| 6,039,302 A | 3/2000 | Cote, Sr. et al. | | 6,840,501 B2 | 1/2005 | Doyle ................ 251/149.1 |
| 6,039,714 A | 3/2000 | Cracauer et al. | | 6,849,061 B2 | 2/2005 | Wagner |
| 6,068,011 A | 5/2000 | Paradis | | 6,896,665 B2 | 5/2005 | Picha et al. |
| 6,079,444 A | 6/2000 | Harris et al. | | 6,897,349 B2 | 5/2005 | Gibbins et al. |
| 6,089,541 A | 7/2000 | Weinheimer et al. | | 6,916,379 B2 | 7/2005 | Shekalim et al. |
| 6,093,154 A | 7/2000 | Burek et al. | | 6,936,031 B2 | 8/2005 | Caleffi |

| | | | | | | |
|---|---|---|---|---|---|---|
| 6,972,001 B2 | 12/2005 | Emig et al. | | 2006/0212000 A1 | 9/2006 | Fangrow ............... 604/247 |
| 6,994,315 B2 | 2/2006 | Ryan et al. | | 2006/0212001 A1 | 9/2006 | Fangrow ............... 604/247 |
| 6,994,325 B2 | 2/2006 | Riedl | | 2006/0212002 A1 | 9/2006 | Fangrow ............... 604/247 |
| 7,004,923 B2 | 2/2006 | Deniega et al. | | 2006/0212003 A1 | 9/2006 | Fangrow ............... 604/247 |
| 7,004,934 B2 | 2/2006 | Vaillancourt ............... 604/533 | | 2006/0264842 A1 | 11/2006 | Fangrow ............... 604/247 |
| 7,008,407 B1 | 3/2006 | Kamp | | 2007/0083157 A1 | 4/2007 | Belley et al. |
| 7,044,441 B2 | 5/2006 | Doyle | | 2007/0083162 A1 | 4/2007 | O'Reagan et al. |
| 7,048,724 B2 | 5/2006 | Grossman et al. | | 2007/0100295 A1 | 5/2007 | Belley et al. |
| 7,048,962 B2 | 5/2006 | Shekalim et al. | | 2007/0100322 A1 | 5/2007 | Venugopalan et al. |
| 7,052,603 B2 | 5/2006 | Schick | | 2007/0235674 A1 | 10/2007 | Vangsness et al. |
| 7,090,191 B2 | 8/2006 | Matkovich et al. | | 2007/0235675 A1 | 10/2007 | Kimball et al. |
| 7,094,218 B2 | 8/2006 | Rome et al. | | 2007/0235676 A1 | 10/2007 | Vangsness et al. |
| 7,100,890 B2 | 9/2006 | Cote, Sr. et al. | | 2007/0255229 A1 | 11/2007 | Kane et al. |
| 7,101,353 B2 | 9/2006 | Lui et al. | | 2007/0260195 A1 | 11/2007 | Bartholomew et al. |
| 7,150,740 B2 | 12/2006 | Bennett et al. | | 2008/0097407 A1 | 4/2008 | Plishka |
| 7,165,568 B2 | 1/2007 | Kessell et al. | | 2008/0177175 A1 | 7/2008 | Mottola et al. |
| 7,179,244 B2 | 2/2007 | Smith et al. | | 2008/0277610 A1 | 11/2008 | Bahner et al. |
| 7,184,825 B2 | 2/2007 | Leinsing et al. | | 2009/0043270 A1 | 2/2009 | Noyce et al. |
| 7,303,553 B2 | 12/2007 | Ott | | 2009/0219353 A1 | 9/2009 | Price et al. |
| 7,311,690 B2 | 12/2007 | Burnett | | 2009/0261130 A1 | 10/2009 | Pittl et al. |
| 7,312,304 B2 | 12/2007 | Coy et al. | | 2010/0030163 A1 | 2/2010 | Carrez et al. |
| 7,314,061 B2 | 1/2008 | Peppel | | 2010/0044609 A1 | 2/2010 | Matsubara |
| 7,320,674 B2 | 1/2008 | Ruddell et al. | | 2011/0009849 A1 | 1/2011 | Christensen et al. |
| 7,341,240 B2 | 3/2008 | Ciesielka | | | | |
| 7,377,915 B2 | 5/2008 | Rasmussen et al. | | FOREIGN PATENT DOCUMENTS | | |
| 7,396,348 B2 | 7/2008 | Newton et al. | | DE | 9105229 | 4/1991 |
| 7,401,703 B2 | 7/2008 | McMichael et al. | | DE | 4311715 | 4/1993 |
| 7,452,346 B2 | 11/2008 | Axelsson | | EP | 0270205 A2 | 6/1988 |
| 7,452,354 B2 | 11/2008 | Bright et al. | | EP | 0829248 A2 | 3/1998 |
| 7,497,848 B2 | 3/2009 | Leinsing et al. | | EP | 1547537 A1 | 6/2005 |
| 7,497,849 B2 | 3/2009 | Fangrow, Jr. | | EP | 1782850 A1 | 5/2007 |
| 7,530,546 B2 | 5/2009 | Ryan et al. | | FR | 2551978 A2 | 3/1985 |
| 7,547,302 B2 | 6/2009 | Porto et al. | | GB | 2394761 A | 5/2004 |
| 7,563,243 B2 | 7/2009 | Mendels | | JP | 2002-049660 A | 2/1990 |
| 7,569,045 B2 | 8/2009 | Deniega et al. | | JP | 2005-115556 A | 5/1993 |
| 7,578,803 B2 | 8/2009 | Rome et al. | | JP | H6-504468 T | 5/1994 |
| 7,584,767 B2 | 9/2009 | Funamura et al. | | JP | H6-66642 | 9/1994 |
| 7,594,910 B2 | 9/2009 | Butts et al. | | JP | 2000-517216 T | 12/2000 |
| 7,611,503 B2 | 11/2009 | Spohn et al. | | JP | 2002-177379 A | 6/2002 |
| 7,614,123 B2 | 11/2009 | Schweikert | | WO | WO 02/04065 | 1/2002 |
| 7,628,779 B2 | 12/2009 | Aneas | | WO | WO 03/018105 | 3/2003 |
| 7,632,260 B2 | 12/2009 | Antoine | | WO | 2005007213 A2 | 1/2005 |
| 7,691,090 B2 | 4/2010 | Belley et al. | | WO | 2005044716 A2 | 5/2005 |
| 7,708,027 B2 | 5/2010 | Yokota et al. | | WO | WO 2005/052366 | 6/2005 |
| 7,766,304 B2 | 8/2010 | Phillips | | WO | 2005099805 A1 | 10/2005 |
| 2002/0002351 A1 | 1/2002 | Cote et al. ............... 604/247 | | WO | 2006004943 A2 | 1/2006 |
| 2002/0153503 A1 | 10/2002 | Newton et al. ............ 251/149.1 | | WO | 2006055288 A2 | 5/2006 |
| 2003/0040769 A1 | 2/2003 | Kelley et al. | | WO | 2006066023 A2 | 6/2006 |
| 2003/0165647 A1 | 9/2003 | Kaneko et al. | | WO | 2007116386 A1 | 10/2007 |
| 2004/0049157 A1 | 3/2004 | Plishka et al. ........... 604/164.09 | | WO | 2009081180 A1 | 7/2009 |
| 2004/0078026 A1 | 4/2004 | Wagner | | WO | 2009118521 A1 | 10/2009 |
| 2004/0082923 A1 | 4/2004 | Field | | WO | 2010028044 A1 | 3/2010 |
| 2004/0116894 A1 | 6/2004 | DeLegge | | WO | 2010091356 A1 | 8/2010 |
| 2004/0209801 A1 | 10/2004 | Brand et al. | | | | |
| 2004/0267163 A1 | 12/2004 | Opie et al. | | OTHER PUBLICATIONS | | |
| 2005/0025816 A1 | 2/2005 | Tanaka | | | | |
| 2005/0090805 A1 | 4/2005 | Shaw et al. ............... 604/523 | | | | |
| 2005/0121638 A1 | 6/2005 | Doyle ............... 251/149 | | | | |
| 2005/0143691 A1 | 6/2005 | Picha et al. | | | | |
| 2005/0203463 A1 | 9/2005 | Lampropoulos | | | | |
| 2005/0203597 A1 | 9/2005 | Yamazaki et al. | | | | |
| 2005/0209572 A1 | 9/2005 | Rome et al. | | | | |
| 2005/0209581 A1 | 9/2005 | Butts et al. | | | | |
| 2005/0251102 A1 | 11/2005 | Hegland et al. ............... 604/500 | | | | |
| 2005/0261636 A1 | 11/2005 | Rome et al. | | | | |
| 2005/0261664 A1 | 11/2005 | Rome et al. | | | | |
| 2005/0267445 A1 | 12/2005 | Mendels | | | | |
| 2005/0281822 A1 | 12/2005 | Cedarbaum et al. | | | | |
| 2006/0009801 A1 | 1/2006 | McGurk et al. | | | | |
| 2006/0015086 A1 | 1/2006 | Rasmussen et al. | | | | |
| 2006/0025816 A1 | 2/2006 | Shelton | | | | |
| 2006/0079853 A1 | 4/2006 | Christensen et al. ......... 604/317 | | | | |
| 2006/0092109 A1 | 5/2006 | Hsu et al. | | | | |
| 2006/0116721 A1 | 6/2006 | Yun et al. | | | | |
| 2006/0118749 A1 | 6/2006 | Ryan et al. | | | | |
| 2006/0129109 A1 | 6/2006 | Shaw et al. | | | | |
| 2006/0200089 A1 | 9/2006 | Lopez et al. | | | | |
| 2006/0211998 A1 | 9/2006 | Fangrow ............... 604/246 | | | | |
| 2006/0211999 A1 | 9/2006 | Fangrow ............... 604/246 | | | | |

Heimlich, H.J., "Valve Drainage of the Pleural Cavity." Diseases of the Chest, vol. 53, No. 3, pp. 282-287, 1968.

U.S. Appl. No. 10/595,450, filed Apr. 20, 2006, Alam et al.

Schweitzer, E.F. et al., "Use of Heimlich Valve in Compact Autotransfusion Device." The Journal of Trauma, vol. 27, No. 5, pp. 537-542, 1987.

Lodi, R., et al., "A New Portable Chest Drainage Device." Ann. Thorac. Surg., vol. 69, pp. 998-1000, 2000.

Campisi, P., et al., "Outpatient Treatment of Spontaneous Pneumothorax in a community Hospital Using a Heimlich Flutter Valve: A Case Series." The Journal of Emergency Medicine, vol. 15, No. 1, pp. 115-119, 1997.

Pope, A., et al., "Fluid Resuscitation:State of the Science for Treating Combat Casualties and Civilian Injuries." National Academy Press, 1999.

Jaskille et al., "A Portable Handpump is Effective in the Evacuation of Hemothorax in a Swine Model of Penetrating Chest Injury." The Journal of Trauma Injury, Infection, and Critical Care, Nov. 2003, pp. 864-868.

"Experimental Plerueodesis in Rabbits Induced by Silver Nitrate or Talc," ASAP, vol. 199, No. 5, p. 1516, May 1, 2001.

"Management of Malignant Pleural Effusions." Am. J. Respir. Crit. Care Med., vol. 165, No. 5, pp. 1987-2001, 2000.
"Pleural Disease-Diagnosis and Management," The Practitioner, p. 412, May 1999.
"Pleurodesis," ASAP, vol. 118, No. 3, p. 577, Sep. 1, 2000.
AstraTech Healthcare, "Premium Wound Drainage Products," http://surgery.astratech.com/Main.aspx? Item=155788&navt=5&navl=82118&nava=81296, copyright 2010, printed Oct. 28, 2010.
Bard Access Systems, Inc., "Poly Per-Q-Cath PICC Catheter with Safety Excallibur Introducer," Instructions for Use, May 2003.
Bard, "Groshong NXT PICC Instructions for Use," Product Brochure, Nov. 2003.
Bilski, T.R., et al., "Battlefield Casualties Treated at Camp Rhino, Afghanistan: Lessons Learned", J. Trauma, vol. 54, No. 5, pp. 814-822, May 2003.
Denver Biomedical, "Pleurx Drainage Kit Catalog No. 50-7500," Instructions for Use.
EP 04811627.1 Supplementary European Search Rerpot dated Oct. 22, 2010.
Groves Jr., "Operations in Urban Enviornments", Military Review, vol. 78, No. 4, Jul./Aug. 1998.
Hewitt at al. "A Management Strategy for Malignancy-Induced Pleural Effusion: Long-term Thoracostomy Drainage." ONF, vol. 14, No. 5, 1987, pp. 17-22.
ICU-USA, "Wound Drainage," www.icu-usa.com/tour/procedures/drains.htm, copyright 1999-2004, printed Oct. 28, 2010.
ISO 10079-2 Medical Suction Equipment—Part 2: Manually Powered Suction Equipment, International Standard Organization 1999 (E).
JP 06-541538 filed Nov. 22, 2004 Summarized Translation of Notice of Rejection (Office Action) dated Mar. 2, 2010.
JP 06-541538 filed Nov. 22, 2004 Summarized Translation of Notice of Rejection (Office Action) dated Jun. 23, 2009.
JP 06-541538 filed Nov. 22, 2004 Summarized Translation of Notice of Rejection (Office Action) dated Oct. 1, 2010.
Light, R.W. et al., "A Single Intrapleural Injection of Transforming Growth Factor-Beta(2) Produces an Excellent Pleurodesis in Rabbits." Am. J. Respir. Crit. Care Med., vol. 162, No. 1, pp. 98-104, 2000.
Light, R.W. et al., "Talc Slurry is an Effective Pleural Sclerosant in Rabbits." Chest, vol. 106, No. 6, pp. 1702-1706, 1995.
Mabry, R.L., et al., "United States Army Rangers in Somalia: An Analysis of Combat Casualties on an Urban Battlefield", J. Trauma. vol. 49, No. 3, pp. 515-529, Sep. 2000.
Medcomp Ash II Split Catha "Features and Benefits" product brochure.
Medcompare, "Drains with Reservoirs," General Surgery Product Matrix, Medompare.com/matrix/1885/Drains-with-Reservoirs.html, copyright 2003-2010, printed Oct. 28, 2010.
Milton, Jr., T.R., "Urban Operations: Future War", Military Review, vol. 74, Issue 2, Feb. 1994.
Montes, J.F. et al., "Influence of Talc Dos on Extrapleural Talc Dissemination after Talc Pleurodesis." Am. J. Respir. Crit. Care Med., vol. 168, No. 3, pp. 348-355, 2003.
Ohm, et al. "Use of Indwelling Pleural Catheter Comparaed with Thorascopic Talc Pleurodesis in the Management of Malignant Pleural Effusions." Division of Thoracic Surgery and Department of Surgery, William Beaumont Hospital, The American Surgeon Mar. 2003, vol. 69, pp. 198-202.
PCT/US04/38937 filed Nov. 22, 2004 Preliminary Report on Patentability dated Jul. 5, 2005.
PCT/US04/38937 filed Nov. 22, 2004 Search Report dated Jul. 5, 2005.
PCT/US2006/037766 filed Sep. 26, 2006 Preliminary Report on Patentability dated Mar. 26, 2008.
PCT/US2006/037766 filed Sep. 26, 2006 Search Report dated Jan. 25, 2007.
PCT/US2006/037766 filed Sep. 26, 2006 Written Opinion dated Mar. 26, 2008.
Tremblay, A. et al., "Single-Center Experience with 250 Tunnelled Pleural Catheter Insertions for Malignant Pleural Effusion." Chest, vol. 129, No. 2, pp. 362-368, 2006.
U.S. Appl. No. 10/595,450, filed Jun. 21, 2007, titled Portable Hand Pump for Evacuation of Fluids, listing Hasan B. Alam, Peter Rhee and Emily Rhee as inventors.
U.S. Appl. No. 10/595,450, filed Jun. 21, 2007 Office Action dated Apr. 9, 2010.
U.S. Appl. No. 10/595,450, filed Jun. 21, 2007 Office Action dated Jul. 7, 2009.
U.S. Appl. No. 10/595,450, filed Jun. 21, 2007 Office Action dated Oct. 1, 2010.
U.S. Appl. No. 10/595,450, filed Jun. 21, 2007 Office Action dated Oct. 30, 2008.
U.S. Appl. No. 11/248,082, filed Oct. 12, 2005 Restriction Requirement dated Jan. 10, 2008.
U.S. Appl. No. 11/248,082, filed Oct. 12, 2005, Notice of Allowance dated Jan. 12, 2010.
U.S. Appl. No. 11/248,082, filed Oct. 12, 2005, Notice of Allowance dated Oct. 15, 2010.
U.S. Appl. No. 11/248,082, filed Oct. 12, 2005, Office Action dated Mar. 30, 2010.
U.S. Appl. No. 11/248,082, filed Oct. 12, 2005, Office Action dated Jun. 29, 2009.
U.S. Appl. No. 11/248,082, filed Oct. 12, 2005, Office Action dated Oct. 30, 2008.
Vargas, F.S. et al., "Comparison of Silver Nitrate and Tetracycline as Pleural Sclerosing Agents in Rabbits." Chest, vol. 108, No. 4, pp. 1080-1083, 1995.
CA 2546434 filed Nov. 22, 2004 Office Action dated Dec. 15, 2010.
EP 04811627.1 filed Nov. 22, 2004 Office Action dated Feb. 23, 2011.
U.S. Appl. No. 11/248,082, filed Oct. 12, 2005 Non-Final Office Action dated Dec. 21, 2010.
U.S. Appl. No. 12/879,673, filed Sep. 10, 2010 Non-Final Office Action dated Feb. 1, 2011.

* cited by examiner

CATHETER CONNECTION SYSTEMS

CROSS-REFERENCE TO RELATED APPLICATIONS

This application claims the benefit of U.S. Provisional Patent Application No. 60/720,443, entitled "CATHETER CONNECTION APPARATUSES AND SYSTEMS," filed Sep. 26, 2005, which is incorporated herein by reference in its entirety.

BACKGROUND

Catheters may be employed for draining fluids from various organs or other locations within a patient. For example, catheters may be used for draining urine, a surgical wound, or any other body location that may be beneficial. Further, it may be desirable to selectively couple and decouple such a catheter to and from a drainage system or other system (e.g., aspiration system, cleansing system, etc.), respectively, for cleaning or for any other suitable reason. Such a connection system can enable an increase in ambulation for the patient and thereby increase quality of life.

BRIEF SUMMARY

One aspect of the instant disclosure relates to a catheter connection system comprising at least two components and a deformable sealing element positioned between the at least two components configured to allow, upon deformation, fluid flow through the at least two components. Another aspect of the instant disclosure relates to a catheter connection system comprising a sealing element positioned between at least two components, wherein the components are coupled to one another by a locking member.

Features from any of the above-mentioned embodiments may be used in combination with one another in accordance with the instant disclosure. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

Advantages of the present invention will become apparent upon review of the following detailed description and drawings, which illustrate representations (not necessarily drawn to scale) of various embodiments of the invention, wherein.

DETAILED DESCRIPTION

One aspect of the instant disclosure relates to apparatuses and systems for selective coupling of a tubular member to another tubular element. Specifically, the instant disclosure contemplates that a catheter may include a connection structure for selectively coupling the catheter to another tubular element by way of a sealing element that forms a seal between the catheter and tubular element.

Figure 1:
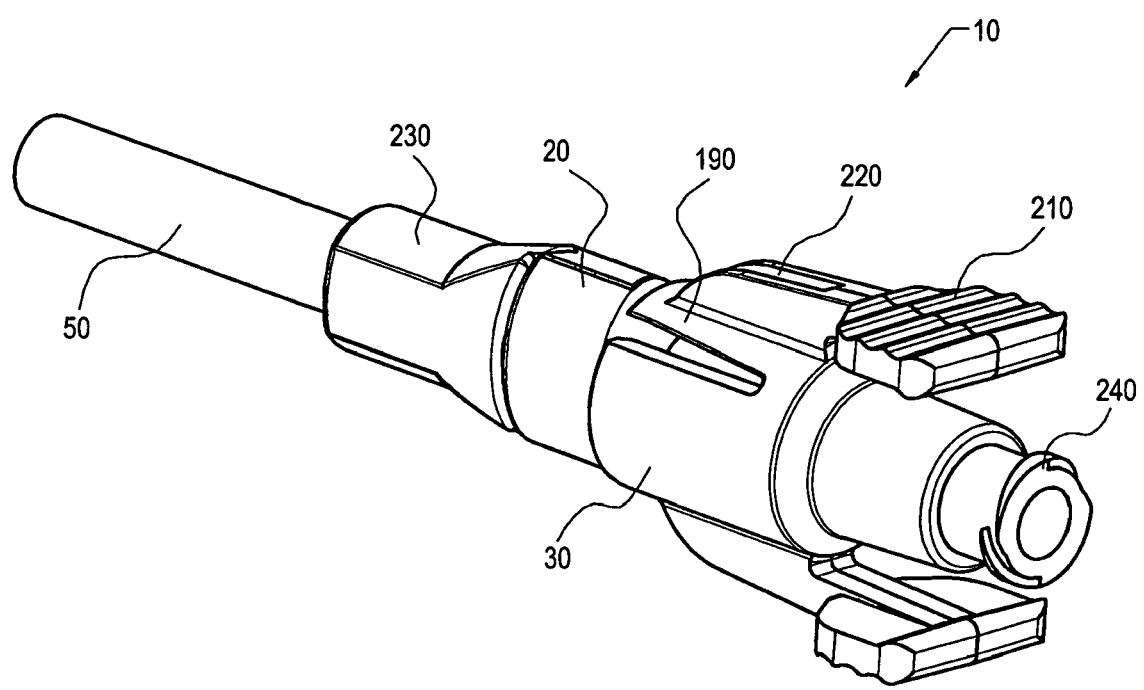
FIG. 1 is a perspective view of one embodiment of a catheter coupling system.
Figure 2:
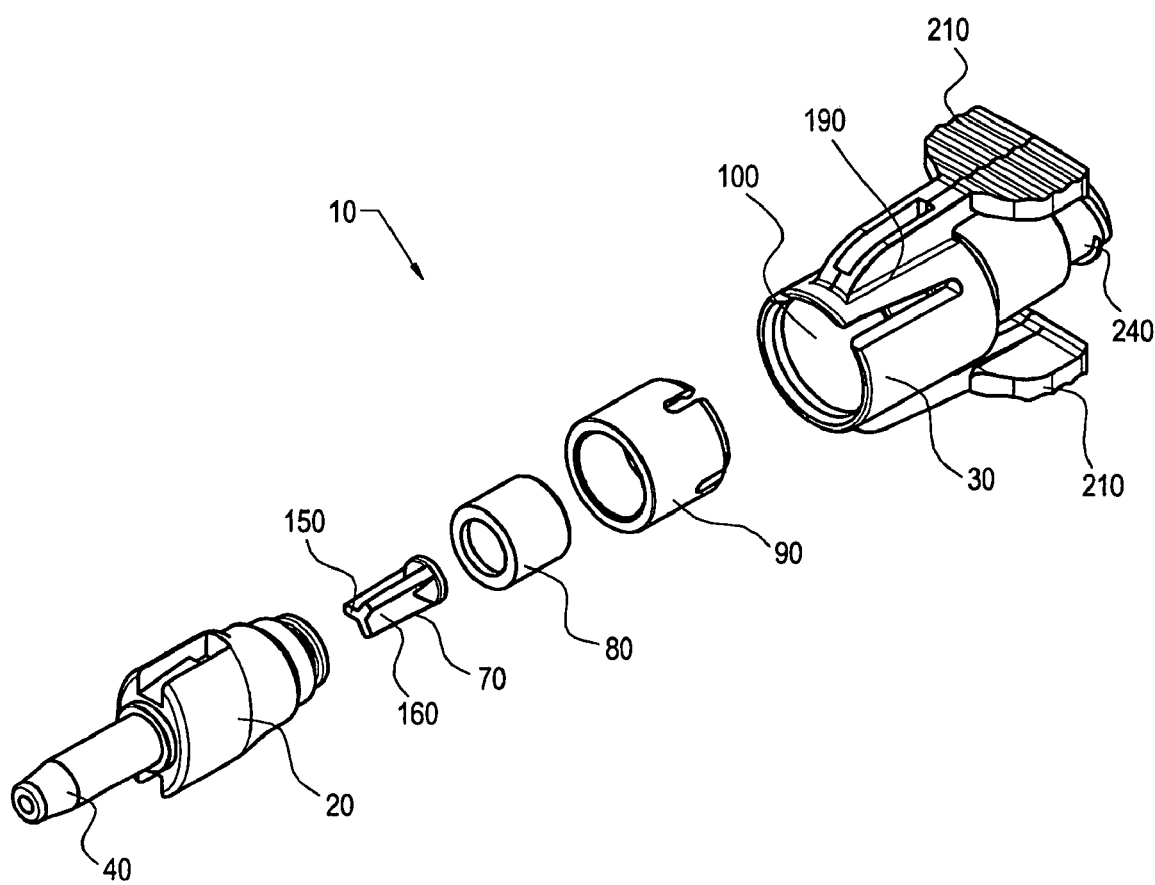
FIG. 2 is an exploded view of the catheter coupling system of FIG. 1.

One aspect of the present invention, as shown in FIG. 1, includes a catheter connection system 10 comprising a catheter hub 20, a coupling member 30, and at least one deformable sealing element positioned within the catheter hub. The deformable sealing element is configured to allow fluid flow through catheter hub 20 upon deformation. As illustrated in FIGS. 1 through 3b, the catheter connector system 10 comprises catheter hub 20 having a cannula 40 on a proximal end thereof sized for insertion into a lumen of a catheter 50. Further, catheter hub 20 has a distal interface 60 having a seal post 70 positioned within a deformable sealing element 80 positioned further within a retention collar 90. As illustrated in FIG. 2, the coupling member 30 includes a cavity 100 for receiving at least a portion of the distal interface 60 of catheter hub 20 and an actuating member 110 for engaging at least a portion of deformable sealing element 80.

Figure 3A:
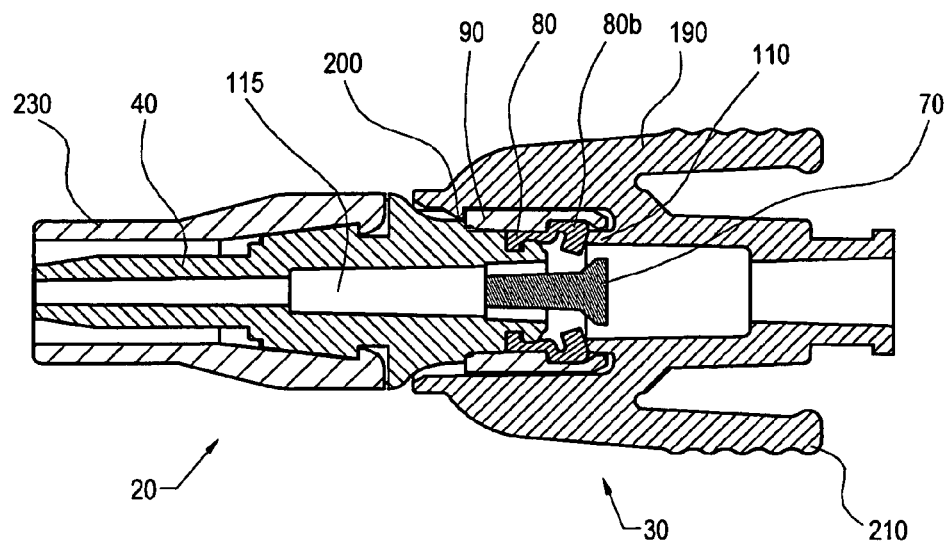
FIG. 3a is a side, cross-sectional view of the catheter coupling system shown in FIG. 1.
Figure 3B:
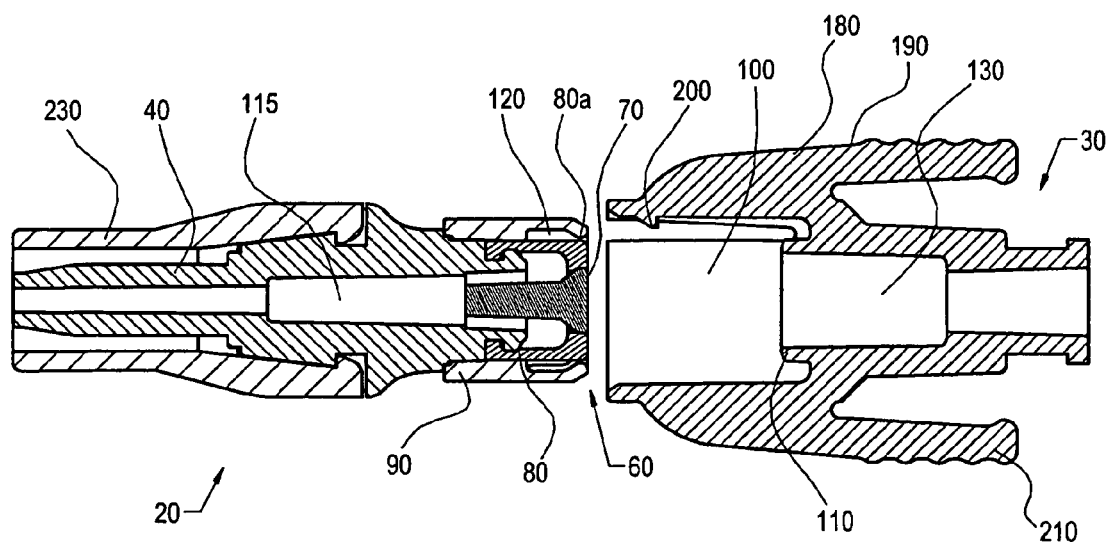
FIG. 3b is a side, cross-sectional view of the catheter coupling system shown in FIG. 1 but with the catheter hub disconnected from the coupling member.

Referring now to FIGS. 3a and 3b, deformable sealing element 80 may abut seal post 70 to effectively seal a bore 115 of catheter hub 20 at one end. In an unbiased position 80a, deformable sealing element 80 creates a seal wherein any fluids attempting to pass through catheter hub 20 are precluded from movement past the seal. When engaged by coupling member 30, deformable sealing element 80 deforms to a biased position 80b thereby allowing fluid to flow through or by deformable sealing element 80 and into coupling member 30. When coupling member 30 is removed from catheter hub 20, deformable sealing element 80 reversibly returns to its unbiased position 80a. The ability of deformable sealing element 80 to reversibly return to its unbiased position 80a permits reuse of catheter hub 20. Furthermore, it advantageously creates a flush surface which facilitates cleaning of distal interface 60 of catheter hub 20. Referring now to FIGS. 3a and 3b, catheter hub 20 can further comprise an open space 120 between retention collar 90 and deformable sealing element 80. Open space 120 provides an area for deformable sealing element 80 to deform when it is engaged by coupling member 30. In one aspect of the invention, retention collar 90 may extend beyond deformable sealing element 80 and seal post 70. Such a configuration may minimize inadvertent deformation of deformable sealing element 80 by a user.

In one embodiment, actuating member 110 can be disposed concentrically within cavity 100. Further, coupling member 30 can be configured with a through-center bore 130 for communicating a fluid from catheter hub 20 through coupling member 30. In an additional embodiment, actuating member 110 comprises a raised surface located within cavity 100 of coupling member 30. The raised surface of actuating member 110 can be shaped to approximate the shape of deformable sealing element 80 such that when coupling member 30 and catheter hub 20 are secured together, as shown in FIG. 3a, actuating member 110 deforms deformable sealing element 80 thereby allowing fluid to pass through catheter hub 20 and into coupling member 30. In another embodiment, actuating member 110 may be configured to deform only a portion of deformable sealing element 80.

Figure 4:
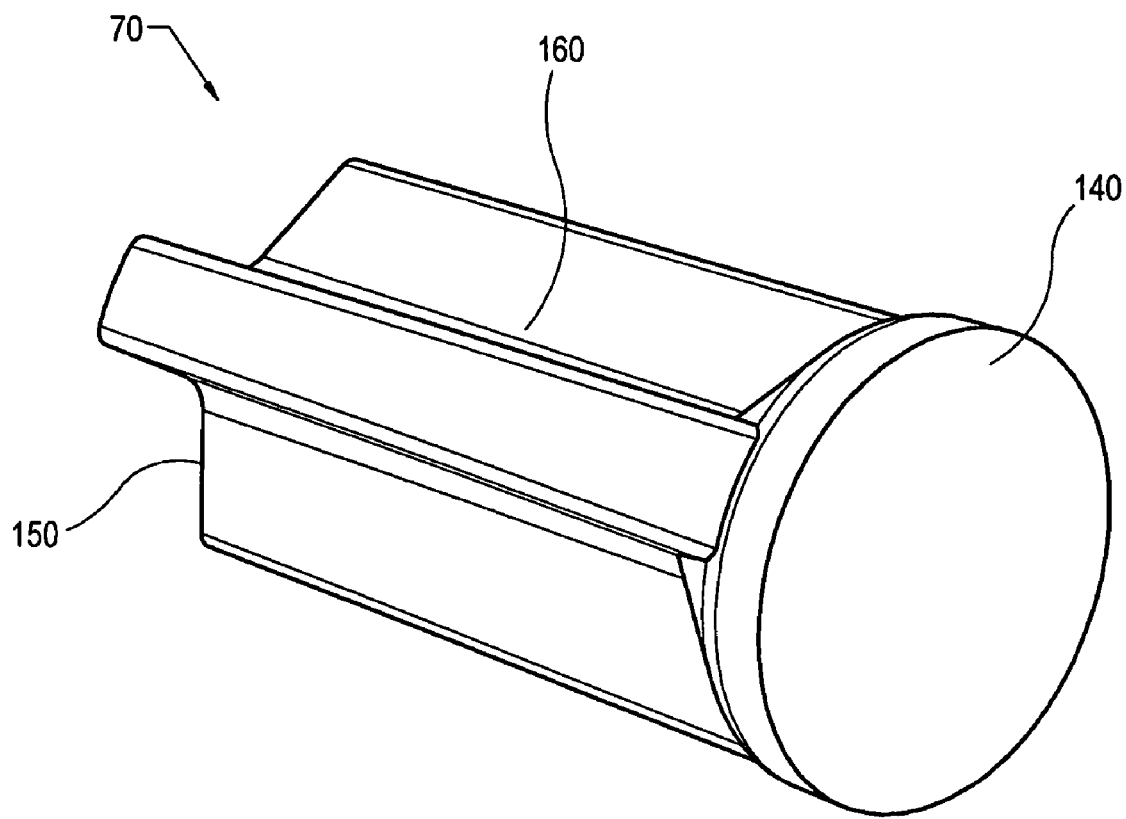
FIG. 4 is a perspective view of one embodiment of a seal post.

In an additional embodiment, seal post 70 may be positioned near deformable selling element 80 to facilitate deformation of deformable sealing element 80 and passage of fluids through catheter hub 20 to coupling member 30. In one embodiment, as shown in FIG. 4, seal post 70 comprises a top planar surface 140 that, when seated in the body of catheter hub 20 and within the center of deformable sealing element 80, creates a flush surface. The body of seal post 70 can be tapered such that the diameter of a distal top planar surface 150 is larger than the diameter of the proximal end 150 of seal post 70. The body of seal post 70 can also comprise at least one channel 160, wherein, when deformable sealing element 80 is deformed, fluid passes through channel 160 of seal post 70 and into coupling member 30. In such a configuration, seal post 70 can be affixed (e.g., adhesively bonded, ultrasonically welded, solvent welded, or otherwise affixed) to the body of catheter hub 20. In another embodiment, seal post 70 may be formed integrally or monolithically with the body of catheter hub 20.

In another embodiment of the present invention, coupling member 30 and catheter hub 20 may be secured together with a locking member 180. The locking member 180 may be any device for securing catheter hub 20 and the coupling member 30 together, for example, a so-called "living hinge clip" or any cantilevered pivoting element. FIGS. 1-3b illustrate a coupling member 30 comprising a biased hinge member 190 integrally formed with the wall of coupling member 30. The hinge member 190 includes an engagement feature 200 configured to engage at least a portion of retention collar 90 of the body of catheter hub 20. Additionally, handles 210 may be formed with hinge member 190 to facilitate removal and attachment of coupling member 30. In one aspect of the invention, as shown in FIGS. 1 and 2, the catheter connection system 10 may comprise an aperture 220 positioned on an outer portion of coupling member 30. Advantageously, aperture 220 allows the user to verify engagement of deformable sealing element 80 by actuating member 110. In another embodiment, the catheter hub 20 also comprises a cover member 230 configured to reduce the likelihood of accidental removal of catheter 50 from cannula 40 of catheter hub 20. A proximal end of coupling member 30 may further comprise a luer fitting 240 configured to receive a device, for example, for vacuum assisted removal of fluids from the patient. In another embodiment, the proximal end of coupling member 30 may be configured for gravity evacuation of fluids from the patient.

The catheter hub 20 and coupling member 30 described above can be formed from any material suitable for connection to any elongated tubular member placed within the corpus of a patient. By way of example, the connector system 10 may be prepared from of any suitable thermo-plastically formed material. The deformable sealing element 80 can be formed from a resilient material that is flexible, inert, and impermeable to fluid, such as silicone or polyurethane.

The above embodiments may be used, for example, in connection with a pleural drainage system. One example of components of a pleural drainage system are disclosed in U.S. patent application Ser. No. 10/595,450 entitled "Portable Hand Pump for Evacuation of Fluids" which is incorporated herein in its entirety. More specifically, the present invention may be used to connect a catheter placed within the corpus of a patient for the purposes of evacuating fluid from the corpus of the patient to a manually-operated pump and a device for storage of the evacuated fluid. The pump may be adapted to connect to an inflow conduit and an outflow conduit. For purposes of clarity, the pump, outflow conduit, and inflow conduit are all downstream from the connection system of the present invention. Near the connection of the inflow conduit, the pump can be provided with a one-way inflow valve that acts to permit flow of fluids from the inflow conduit into the interior of the pump but limits or restricts any back flow of the same into the inflow conduit. Similarly, near the connection of the outflow conduit, a one-way outflow valve permits flow of fluids out of the pump interior and into and through a lumen of the outflow conduit. This outflow one-way valve also serves to limit or restrict the back flow of fluids from the outflow conduit into the pump interior.

While certain embodiments and details have been included herein for purposes of illustrating aspects of the instant disclosure, it will be apparent to those skilled in the art that various changes in the systems, apparatuses, and methods disclosed herein may be made without departing from the scope of the instant disclosure, which is defined, in part, in the appended claims. The words "including" and "having," as used herein including the claims, shall have the same meaning as the word "comprising."

The invention claimed is:

1. A method for coupling to a catheter, the catheter including a catheter hub, the catheter hub including a deformable sealing element, the method comprising:

engaging the catheter hub with a coupling member, wherein the catheter hub is initially sealed prior to engagement with the coupling member by the deformable sealing element being in contact with a sealing post longitudinally fixed relative to the catheter hub, and is opened after engagement with the coupling member by the deformable sealing element being out of contact with the sealing post; and contacting an actuating member of the coupling member with the deformable sealing element without penetrating a proximal opening thereof such that the deformable sealing element is opened to enable fluid flow therethrough, an engagement feature of the coupling member releasably locking with an extended surface of the catheter hub such that the coupling member is longitudinally aligned with the catheter hub.

2. The method for coupling as defined in claim 1, wherein the engagement feature of the coupling member is included on a hinge arm and wherein engaging the catheter hub with the coupling member further comprises:

axially moving the catheter hub and the coupling member toward each other such that the engagement feature on the hinge arm of the coupling member hingedly locks with the extended surface of the catheter hub.

3. The method for coupling as defined in claim 2, further comprising:

manually disengaging the catheter hub from the coupling member when engagement therebetween is no longer desired.

4. The method for coupling as defined in claim 3, wherein manually disengaging the catheter hub from the coupling member further comprises:

pressing the hinge arm of the coupling member so as to separate the engagement feature thereof from the extended surface of the catheter hub; and pulling the catheter hub and coupling apart from one another.

5. The method for coupling as defined in claim 1, wherein the extended surface of the catheter hub includes an annular ledge.

6. The method for coupling as defined in claim 1, wherein engaging the catheter hub with a coupling member further comprises:

engaging the catheter hub with the coupling member such that a fluid pathway is defined therebetween.

7. The method for coupling as defined in claim 1, further comprising inserting the catheter hub into a cavity of the coupling member, the cavity defined by a generally cylindrical wall comprising two slits to create the engagement feature.

8. The method for coupling as defined in claim 1, further comprising inserting the catheter hub into a cavity of the coupling member, the actuating member comprising a raised surface within the cavity shaped to approximate the shape of the deformable sealing element.

9. The method for coupling as defined in claim 1, wherein the deformable sealing element circumferentially surrounds a portion of the sealing post.

10. The method for coupling as defined in claim 1, wherein contacting the actuating member with the deformable sealing element further comprises the actuating member contacting an end of the deformable sealing element such that when the coupling member is engaged with the catheter hub, the actuating member longitudinally displaces a portion of the deformable sealing element without passing an end surface of the deformable sealing element.

* * * * *